United States Patent [19]

Stewart et al.

[11] 4,237,724
[45] Dec. 9, 1980

[54] DETECTION OF BATCH INTERFACES IN PIPELINES

[75] Inventors: Thomas L. Stewart, Houston; Joe O. Esparza, Katy, both of Tex.

[73] Assignee: Shell Oil Company, Houston, Tex.

[21] Appl. No.: 35,673

[22] Filed: May 3, 1979

[51] Int. Cl.³ .................. G01N 11/00; G01R 27/26
[52] U.S. Cl. .................................................. 73/53
[58] Field of Search ............... 73/61.1 R, 61 R, 53; 324/61 R; 210/402

[56] References Cited

U.S. PATENT DOCUMENTS

| | | | |
|---|---|---|---|
| 2,654,067 | 9/1953 | Bruce | 73/53 X |
| 2,670,849 | 3/1954 | Dunmire | 210/402 X |
| 2,678,133 | 5/1954 | Thayer et al. | 210/402 X |
| 2,906,949 | 9/1959 | Shawhan | 73/53 X |
| 3,770,020 | 11/1973 | Tamura et al. | 73/53 X |

*Primary Examiner*—Gerald Goldberg
*Assistant Examiner*—Joseph W. Roskos

[57] ABSTRACT

Interfaces are detected in pipeline batching by means of a capacitance cell for determining dielectric constants. The batch fluid may be purified by a centrifugal filter to allow identification of the batch fluid by dielectric constant.

13 Claims, 1 Drawing Figure

DETECTION OF BATCH INTERFACES IN PIPELINES

BACKGROUND OF THE INVENTION

It is standard practice to send batches of different fluids in the same pipeline, for example, different crude oils or gasolines, diesel fuel, kerosene, and furnace oil. Gravitometers which continuously weigh small fixed volumes of the fluids flowing in the pipeline are utilized to detect the interface in the pipeline between different fluid batches. Difficulties arise where the specific gravities of adjacent batches are similar, which is not uncommon, for example similar fluids from different shippers, or two brands of gasoline. Accordingly, in such instances, it is desirable to have some interface detection means available which does not rely upon specific gravities.

Further difficulties may arise in the use of gravitometers when it is desirable not only to detect the interface between batches, but also to identify the oil or other fluid comprising a batch. Impurities in the batch such as water can prevent correlations between the specific gravity of the batch and the identifying specific gravity of the pure fluid of the batch.

Prior art considered pertinent to the present invention includes U.S. Pat. Nos. 3,546,926 and 3,189,180 and co-pending application Ser. No. 905,261, filed May 12, 1978 now U.S. Pat. No. 4,184,952.

DESCRIPTION OF PREFERRED EMBODIMENTS

Figure 1:
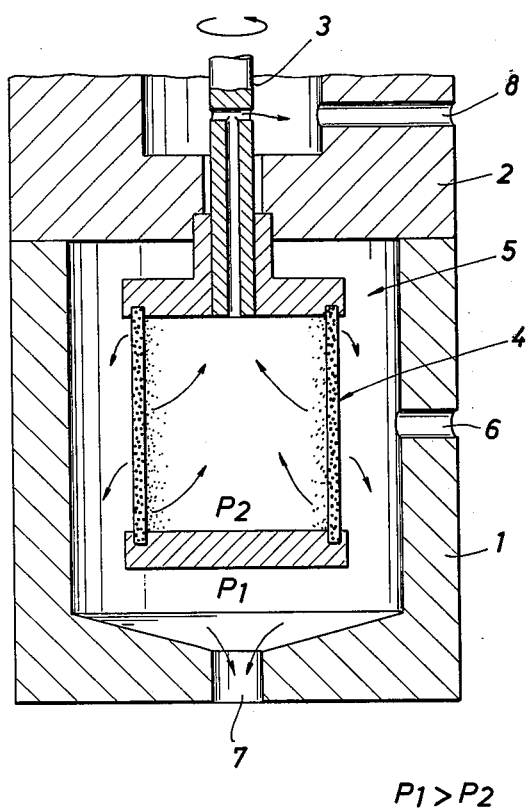
FIG. 1 is a schematic diagram of a batch fluid separator.

The present invention is particularly pertinent to batching in crude oil or refined hydrocarbon pipelines. However, it is also applicable to pipelines carrying fluid chemicals other than hydrocarbons, e.g. chemicals such as chlorine or carbon dioxide.

In order to detect the interface between liquid batches in a pipeline, the present invention utilizes a capacitance cell to measure the dielectric strength of the material flowing between its plates. The dielectric constant of most crude oils from any one particular formation remains unchanged but in contrast, the dielectric constant of crude oils from different formations can vary considerably. And of course, the dielectric constant of various other hydrocarbons and liquids can vary substantially. Hence, the capacitance cell is ideal for detecting a change of material flowing in a pipeline, i.e., an interface between different batches of material. As above mentioned, it is now common practice in the art to rely upon a gravitometer for detecting batch interfaces but difficulties arise when the specific gravities of adjacent batches are similar, which is not uncommon. While it is even less common that dielectric constants of adjacent batches would be similar, it is within the purview of the present invention to use both gravitometers and capacitance cells in unison, which would eliminate failure to detect an interface except in the rare instance where both the specific gravity and the dielectric constant of adjacent batches would be similar.

Preferably, the capacitance cell is disposed within the pipeline and powered by means outside the pipeline. The change of capacitance of the fluid or fluids flowing within the pipeline is continuously or at least periodically monitored by the cell and recorded on a time correlated chart or table. From review of such recording means, it can be determined quite accurately when or if an interface between batches has passed or is passing.

In some instances it may be desirable not only to detect the interface between batches, but also to identify the oil or other fluid comprising the batch. Impurities in the batch such as water or sediment (BS & W) can prevent direct identification of the batch since the dielectric constant of the impure batch may be different from the dielectric constant of the pure batch. To clean up a sample of the batch for identification, the present invention provides apparatus for separating impurities from the sample.

The separator of the invention is enclosed by a chamber housing 1 affixed to a bearing and seal housing 2 by bolts (not shown). Ball bearings and a mechanical seal (not shown) position a hollow drive shaft 3 within the bearing and seal housing. The hollow drive shaft is terminated at one end by a porous filter (e.g. stainless steel filter) which resides in a chamber 5 formed by housing 1 and containing a sample of the batch fluid which is admitted thereinto through inlet port 6. When the apparatus is in operation, underflow exits from chamber 5 via port 7 as shown by the direction of the downward arrows. Batch fluid passes through the porous filter 4 into the hollow drive shaft 3 and exits via clean batch fluid exit 8 as shown by the direction of the upward arrows. The hollow drive shaft 3 rotates the porous filter to separate the entering stream into clean batch fluid and impurities which are spun out. Batch fluid in chamber 5 is at a greater pressure than clean batch fluid in port 8 which is filtered by passing through filter 4 and centrifuged inside the filter.

The fluid stream entering via port 6 containing, for example, emulsified water, free water and suspended sediment is forced into the housing 1 at a flow rate which can be varied up to 5,000 ml per minute or more. Total flow of the impure stream, as well as flow of the pure stream, are both related to physical size of the device. Permissible flow of the dry stream is proportional to the filter area, radius, and RPM squared. Flow of the impure stream is limited only by the piping and port sizes and the cross-sectional area of the annulus. The influx may be directed tangential to and opposing the direction of rotation of the porous filter 4. This condition creates a continuous additional shear force upon the outer surface of the filter, which aids in preventing particles from accumulating on and clogging the filter. In addition, the centrifugal force due to the high angular velocity of the filter forces the denser particles (e.g., water, free water and sediment) outward toward the wall of the housing 1 and down through the underflow exit 7. The pressure differential between the housing and the inside of the filter tends to force the resident fluid through the filter pores and up through the hollow drive shaft 3 wherefrom it is discharged via port 8 to a pure batch fluid chamber (not shown).

Variables affecting use of the invention are speed of rotation of filter 4, width of annulus between filter 4 and housing 1, filter pore size, pressure differential between housing 1 and the interior of filter 4, entrance flow rate at port 6, direction of the influx batch fluid through port 6, and temperature and viscosity of the influx batch fluid.

Several types of filters are available which are suitable for use with the invention. Specifically acceptable for use is a 20 micron pore filter manufactured by AMF CUNO as item number 50387-01-41-0201.

The pore size of such filters ranges from about 2 to about 55 microns or more. The annulus width between the filter and housing can vary from almost nil to several inches or more, while the pressure differential between the housing and interior of the filter may vary from almost nil to about 70 psi or more. Differential pressure required is determined by centrifugal force and the resistance imposed by the filter and is limited by the physical strength of the filter to withstand high differential pressures.

Entrance flow rates range from down to almost 0 to 50,000 ml/min or more while temperature of the influx liquid batch sample varies from about 0° C. to about 40° C. or more. The speed of rotation of the filter ranges from about 100 rpm or less to 10,000 rpm or more. Preferably, the filter is rotated by an electric motor with a continuous range of variable speed drive.

I claim as my invention:

1. A method for detecting the interface between batches of different fluids in a pipeline, the fluids all containing BS&W, and for identifying each batch fluid comprising, continuously withdrawing a sample of the batch fluid from the pipeline, rotating a fluid pervious inner chamber within an outer chamber, admitting the sample of batch fluid to the outer chamber, pressuring the sample fluid from the outer chamber into the inner chamber, allowing centrifugal force in the inner chamber to force more-dense sample fluid including BS&W back into the outer chamber, separately withdrawing less-dense sample fluid essentially free of BS&W from the inner chamber, identifying the dielectric constant of the less-dense sample fluid and identifying the batch fluid by correlating the identified dielectric constant to a dielectric constant of a known fluid, and correlating change of dielectric constant to the passing of an interface between batches of different fluids.

2. The method of claim 1 wherein the dielectric constant is determined by a capacitance cell.

3. The method of claim 1 wherein the inner chamber is a filter and the fluid contains particles too large to pass through the filter.

4. The method of claim 1 wherein the filter has a porosity of from 2 to 55 microns or more.

5. The method of claim 4 wherein the inner chamber is rotated at from 100 to 10,000 rpm.

6. The method of claim 1 wherein the less dense fluid is withdrawn through a hollow drive shaft which rotates the inner chamber.

7. The method of claim 1 wherein the fluid is introduced into the outer chamber at any angle between radially and approximately tangentially to the inner chamber.

8. The method of claim 7 wherein the direction of flow of the fluid, when introduced into the outer chamber, may either oppose or go with the direction of rotation of the inner chamber.

9. The method of claim 8 wherein the flow rate of the fluid varies up to 5,000 milliliters per minute.

10. The method of claim 1 wherein the pressure differential between the inner and outer chambers varies up to 70 psi.

11. A method for identifying a pipeline fluid containing BS&W comprising, withdrawing a sample of the fluid from the pipeline, rotating a fluid pervious inner chamber within an outer chamber, admitting the sample of fluid to the outer chamber, pressuring the sample fluid from the outer chamber into the inner chamber, allowing centrifugal force in the inner chamber to force more-dense sample fluid including BS&W back into the outer chamber, separately withdrawing less-dense sample fluid essentially free of BS&W from the inner chamber, identifying the dielectric constant of the less-dense sample fluid and identifying the pipeline fluid by correlating the identified dielectric constant to a dielectric constant of a known fluid.

12. The method of claim 11 wherein the identified dielectric constant is determined by a capacitance cell.

13. The method of claim 11 wherein the pipeline fluid is a batch fluid and a sample of the batch fluid is continuously removed from the pipeline, separated from BS&W, and identified.

* * * * *